US005573996A

United States Patent [19]
Inoue

[11] Patent Number: 5,573,996
[45] Date of Patent: Nov. 12, 1996

[54] REVERSIBLE HEAT-SENSITIVE RECORDING MEDIUM AND MAGNETIC CARD USING THE SAME

[75] Inventor: Yasushi Inoue, Osaka, Japan

[73] Assignee: Nitto Denko Corporation, Osaka, Japan

[21] Appl. No.: 404,562

[22] Filed: Mar. 15, 1995

[30] Foreign Application Priority Data

| Mar. 15, 1994 | [JP] | Japan | 6-71421 |
| Apr. 22, 1994 | [JP] | Japan | 6-107525 |
| Jul. 19, 1994 | [JP] | Japan | 6-189852 |

[51] Int. Cl.⁶ .................................................. B41M 5/36
[52] U.S. Cl. ............... 503/208; 428/195; 428/216; 428/694 R; 428/913; 428/914; 503/201; 503/217; 503/226
[58] Field of Search ................................. 503/201, 204, 503/226; 428/195, 694 R, 913, 914, 212, 213, 215, 216

[56] References Cited

U.S. PATENT DOCUMENTS 5,219,820  6/1993  Morohoshi et al. ............... 503/204

FOREIGN PATENT DOCUMENTS

| 0535930 | 4/1993 | European Pat. Off. | 503/201 |
| 0567012 | 10/1993 | European Pat. Off. | 503/201 |
| 2-24339 | 2/1990 | Japan | 503/201 |

*Primary Examiner*—Bruce H. Hess
*Attorney, Agent, or Firm*—Sughrue, Mion, Zinn, Macpeak & Seas

[57] ABSTRACT

A reversible heat-sensitive recording medium comprising a transparent substrate having a reversible heat-sensitive recording layer formed on one surface of the substrate and having a colored layer formed on the other surface of the substrate, wherein the reversible heat-sensitive recording layer contains organic low molecular weight materials and a crosslinked resin matrix.

5 Claims, 2 Drawing Sheets

○ EXAMPLE 1 : PRINTING
● EXAMPLE 1 : ERASING
△ COMPARATIVE EXAMPLE 8 : PRINTING
▲ COMPARATIVE EXAMPLE 8 : ERASING

REVERSIBLE HEAT-SENSITIVE RECORDING MEDIUM AND MAGNETIC CARD USING THE SAME

FIELD OF THE INVENTION

The present invention relates to a reversible heat-sensitive recording medium which can reversibly repeat to form and erase images by a heating means such as a thermal head, etc., and to a magnetic card using the recording medium.

BACKGROUND OF THE INVENTION

Recently, with the spread of thermal heads, the demand for heat-sensitive recording media has been suddenly increased. In particular, in prepaid cards which are being rapidly spreading in the field of communications, transportations, distributions, etc., it has frequently be practiced to indicate a magnetic information on a card as a visible information. Such magnetic cards have been widely used as highway cards, prepaid cards in department stores, supermarkets, etc., JR (Japanese Railways Co.) orange cards, etc.

However, in such a recording medium, the area on which a visible information can be indicated is limited and thus, for example, in the case of a large amount of a prepaid card, it sometimes happens that when the balance is additionally indicated, the additional information cannot be indicated. In such a case, a new card is usually reissued to cope therewith, which causes a problem of increasing a cost.

To overcome such a problem, it has been investigated on a reversible recording medium capable of repeatedly recording and erasing an information on the same area. If such a recording medium is used, an old unnecessary information can be erased and a new information can be indicated, whereby it becomes unnecessary to reissue a new card due to lacking in an additional area to be indicated. Further, by using such a recording medium as, for example, a facsimile paper, resorces can be saved, which contributes to overcome the environmental problem.

Hitherto, as a heat-sensitive recording medium capable of reversibly recording and erasing an information, a recording medium having a heat-sensitive layer formed by dispersing an organic low molecular weight material such as a higher alcohol, a higher fatty acid, etc., in a resin matrix such as polyvinyl chloride, a vinyl chloride-vinyl acetate copolymer, polyester, polyamide, etc., is proposed as disclosed in JP-A-54-119377, JP-A-55-154198, and JP-A-2-1363 (the term "JP-A" as used herein means an "unexamined published Japanese patent application").

The principle of the formation and erasion of images in such a reversible heat-sensitive recording medium is in the difference of a transparency of the heat-sensitive layer when the heat-sensitive layer is heated to a different temperature and returned to normal temperature. That is, when such a recording medium is heated to a definite temperature and returned to normal temperature, the heat-sensitive layer shows a transparent state, but when the recording medium is heated to other temperature than the above definite temperature and returned to normal temperature, the heat-sensitive layer shows a white turbid state. For recording to such a heat-sensitive recording medium, a thermal head is used and for erasing the recorded information, a heat roll, a hot stamp, a thermal head, etc., is used.

Since the white turbid state of the recording medium described above is the state of utilizing the scattering of light, the hiding property is low and the contrast is poor. To overcome the problem, it is proposed to form a metal reflective layer or a colored layer on the surface of the reversible heat-sensitive recording layer, i.e., between the recording layer and a substrate.

However, when a metal reflective layer is formed on the surface of the reversible heat-sensitive recording layer, since all the light transmitting through the transparent portion is reflected, the white turbid portion formed by printing becomes difficult to confirm, depending on a seeing angle.

When a black or blue colored layer is formed on the surface of the reversible heat-sensitive recording layer, the scattered light from the white turbid portion is less and a sufficient contrast is not obtained. As a result, it becomes necessary to increase the thickness of the reversible heat-sensitive recording layer, which results in increasing the energy required for recording, and when recording is repeated, the early deterioration of the recording layer becomes severe.

Furthermore, for improving the contrast at the white turbid portion, a method of coloring a substrate and then forming a reversible heat-sensitive recording layer on the substrate through an air layer is proposed as described in JP-A-4-220400, but in this method, there are problems that the production method is complicated and the cost is increased.

SUMMARY OF THE INVENTION

As a result of extensive investigations to overcome the problems in the conventional techniques, it has been found that the problems described above can be overcome by forming a reversible heat-sensitive recording layer on one surface of a substrate and forming a colored layer on the other surface of the substrate. The present invention has been accomplished based on this finding.

The present invention provides a reversible heat-sensitive recording medium comprising a substrate, a reversible heat-sensitive recording layer formed on one surface of the substrate, and a colored layer formed on the other surface of the substrate, wherein the reversible heat-sensitive recording layer contains an organic low molecular weight material and a crosslinked resin matrix.

In the conventional reversible heat-sensitive recording medium wherein a metal vapor-deposited layer having been subjected to a mirror-surface luster treatment or a colored layer with a color ink is formed on the heat-sensitive recording layer thereof (i.e., between the recording layer and the substrate), a print is difficult to see depending on a seeing angle, or the contrast is low. On the other hand, in the reversible heat-sensitive recording medium of the present invention, reflected light from the substrate also exists, whereby the angle dependency as in the conventional recording medium does not occur. Further, in the recording medium of the present invention, the number of the production steps is less than the conventional cases, whereby the cost for the recording medium can be reduced.

DETAILED DESCRIPTION OF THE INVENTION

The recording medium of the present invention is described in more detail below.

Figure 1:
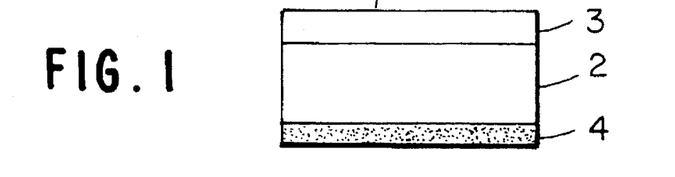
FIG. 1 is a schematic cross sectional view showing one example of the reversible heat-sensitive recording medium of the present invention.

FIG. 1 is a schematic cross sectional view showing one example of the recording medium of the present invention. In FIG. 1, the reversible heat-sensitive recording medium 1 is composed of a substrate 2, a reversible heat-sensitive recording layer 3 formed on one surface of the substrate, and the colored layer 4 formed on the other surface of the substrate 2.

The substrate used in the present invention is a transparent plastic film such as a polyethylene terephthalate film, a polypropylene film, etc., and the thickness of the substrate is at least 30 μm, and preferably at least 50 μm. This is because white turbid portions (recorded portions) of the reversible heat-sensitive recording layer are more clearly seen since light is properly scattered in the transparent plastic film, and where the thickness of the transparent plastic film is smaller than 30 μm, such an effect is not obtained.

The reversible heat-sensitive recording layer comprises a thermally crosslinked resin matrix containing an organic low molecular weight material. The resin matrix forms a layer which retains the uniformly dispersed organic low molecular weight material and greatly affects the transparency of the recording layer when the layer is transparent. For this reason, the resin matrix preferably is a resin which has a high transparency, is mechanically stable, and is excellent in a film-forming property. Further, in the present invention, the reversible heat-sensitive recording layer is thermally crosslinked to improve the heat resistance of the recording layer.

Examples of the resin matrix used for such a heat-sensitive recording layer are vinyl chloride copolymers such as a vinyl chloride-vinyl acetate-vinyl alcohol copolymer, a vinyl chloride-acrylic acid copolymer, a vinyl chloride-vinyl acetate-maleic anhydride copolymer, a vinyl chloride-vinyl acetate-hydroxyalkyl acrylate copolymer, an epoxy-denatured vinyl chloride-vinyl acetate copolymer, etc.; thermoplastic resins such as an epoxy resin, a phenoxy resin, an acrylic resin, etc.; and thermosetting resins. Those resin matrixes can be used alone or as mixtures thereof.

Examples of a crosslinking agent which is used to thermally crosslink the resin matrix are amino resins such as hexamethoxymethylmalanine, benzoguanamine, a urea resin, etc.; isocyanates such as 2,4-/2,6-tolylene diisocynate, 4,4'-diphenylmethane diisocyanate, etc.; amines such as polymethylenediamine, diaminophenylmethane, diaminophenylsulfone, o-toluidine, benzyldimethylamine, etc.; and epoxy compounds such as triglycidyl isocyanate, 3,4-epoxycyclohexylmethyl-3,4-epoxycyclohexane carboxylate, an epoxylated melamine resin, etc. Other crosslinking agent such as acid anhydrides, methylacrylamide glycolate methyl ether, etc., may be used. The crosslinking agent may be used together with a catalyst for accelerating the reaction.

The amount of the crosslinking agent added is from 0.5 to 50% by weight, and preferably from 1.0 to 30% by weight, based on the weight of the resin matrix. If the amount of the crosslinking agent is less than 0.5% by weight, crosslinking is insufficient and the deterioration-inhibiting effect for the repeated use of the recording medium is insufficient. If the amount of the crosslinking agent is more than 50% by weight, the white turbidity is lowered by the repeated utilization of the recording medium since the crosslinking agent shows a plasticizing action, and finally a sufficient contrast is not obtained.

The organic low molecular weight compounds used for the reversible heat-sensitive recording medium of the present invention comprise at least two components. The following components:

(A) at least one compound selected from a higher fatty acid having at least 16 carbon atoms and a ketone having a melting point of at least 50° C., and (B) at least one compound selected from an aliphatic saturated dicarboxylic acid and a sulfide represented by the following general formula:

$$HOOC(CH_2)_m\text{-}S\text{-}(CH_2)_nCOOH$$

wherein m and n each represents an integer of from 1 to 5 are preferably used.

Examples of the above compounds used in the present invention are shown below.

Organic Low Molecular Weight Material

A higher fatty acid having at least 16 carbon atoms and an aliphatic ketone compound having a melting point of at least 50° C. are used as the organic low molecular weight material.

Examples of the higher fatty acid having at least 16 carbon atoms and the aliphatic ketone compounds having a melting point of at least 50° C., which can be used in the present invention, are illustrated below.

Specific examples of the higher fatty acid having at least 16 carbon atoms which can be used in the present invention are palmitic acid, margaric acid, stearic acid, nonadecanoic acid, eicosanic acid, heneicosanoic acid, behenic acid, lignoceric acid, pentacosanoic acid, cerotic acid, heptacosanoic acid, montanic acid, triacontanoic acid, nonacosanoic acid, melissic acid, 2-heptadecenoic acid, 2-hexadecenoic acid, trans-2-octadecenoic acid, cis-2-octadecanoic acid, trans-4-octadecenoic acid, trans-3-hexadecenoic acid, cis-6-octadecenoic acid, elaidic acid, vaccenic acid, 11-icosenoic acid, erucic acid, 13-docosenoic acid (trans), brassidic acid, selacholeic acid, trans-selacholeic acid, trans-8-octadecadienoic acid, trans-10-octadecadienoic acid, linoelaidic acid, α-eleostearic acid, β-eleostearic acid, pseudoeleostearic acid, and 12,20-heneicosadienoic acid.

Specific examples of the ketone compound having a melting point of at least 50° C. are as follows.

1) Dialkyl ketones represented by the general formula: $CH_3(CH_2)_{n-1}CO(CH_2)_{n-1}CH_3$ wherein $n \geq 8$ 2) Methyl alkyl ketones represented by the general formula: $CH_3CO(CH_2)_{n-3}CH_3$ wherein $n \geq 17$ 3) Phenyl alkyl ketones represented by the general formula: $C_6H_5CO(CH_2)_{n-1}CH_3$ wherein $n \geq 10$ 4) Macrocyclic ketones represented by the general formula:

wherein n ≥ 10

5) Symmetric α-diketones represented by the general formula: RCOCOR wherein R=$C_nH_{2n+1}$ wherein n ≥ 7

6) Acyloins represented by the general formula: RCH(OH)COR wherein R=$C_nH_{2n+1}$ wherein n ≥ 7

7) Cyclcic acyloins represented by the general formula:

wherein n ≥ 12

8) Ketene dimers represented by the general formula:

wherein R=$C_nH_{2n+1}$ wherein n ≥ 14

The melting point of the organic low molecular weight material (A) used in the present invention is preferably at least 50° C. If the melting point of the organic low molecular weight material (A) is lower than 50° C., the crystal state of a low molecular weight material in the recording layer formed becomes unstable at room temperature and the energy value required for recording is changed during the storage, whereby the energy region for making transparency is shifted and it becomes undesirably impossible to erase with a definite energy.

Organic Low Molecular Weight Material (B)

A compound compatible with the resin matrix is used as the organic molecular material (B).

Aliphatic saturated dicarboxylic acids and sulfides represented by the following general formula HOOC $(CH_2)_m$-S-$(CH_2)_n$COOH wherein m and n each represents an integer of from 1 to 5 are preferably used as those compounds.

Specific examples of the aliphatic dicarboxylic acid [general formula: HOOC$(CH_2)_{n-2}$COOH] are the following compounds.

| Number of n | Name of material |
|---|---|
| 2 | Oxalic acid |
| 3 | Malonic acid |
| 4 | Succinic acid |
| 5 | Glutaric acid |
| 6 | Adipic acid |
| 7 | Pimelic acid |
| 8 | Suberic acid |
| 9 | Azelaic acid |
| 10 | Sebacic acid |
| 11 | Undecane dicarboxylic acid |

-continued

| Number of n | Name of material |
|---|---|
| 12 | Dodecanoic acid |
| 13 | Tridecane dicarboxylic acid |
| 14 | Tetradecane dicarboxylic acid |
| 15 | Pentadecane dicarboxylic acid |
| 16 | Hexadecane dicarboxylic acid |
| 17 | Heptadecane dicarboxylic acid |
| 18 | Octadecane dicarboxylic acid |
| 19 | Nonadecane dicarboxylic acid |
| 20 | Eicosane dicarboxylic acid |
| 21 | Heneicosane dicarboxylic acid |
| 22 | Docosane dicarboxylic acid |
| 23 | Tricosane dicarboxylic acid |
| 24 | Tetracosane dicarboxylic acid |
| 26 | Hexacosane dicarboxylic acid |
| 30 | Nonacosane dicarboxylic acid |
| 34 | Dotriacontane dicarboxylic acid |

Specific examples of the sulfide represented by the general formula HOOC$(CH_2)_m$-S-$(CH_2)_n$COOH wherein m and n each represents an integer of from 1 to 5 are (1,1'-dicarboxy)dimethyl sulfide, (2,2'-dicarboxy)diethyl sulfide [thiodipropionic acid], (3,3'-dicarboxy)dipropyl sulfide, (1,2'-dicarboxy)methylethyl sulfide, (1,3'dicarboxy)methylpropyl sulfide, (1,4'-dicarboxy)methylbutyl sulfide,(2,3'-dicarboxy)ethylpropylsulfide,(2,4'-dicarboxy)ethylbutyl sulfide, and (5,5'-dicarboxy)dipentyl sulfide. In these sulfides, thiodipropionic acid is particularly preferred.

The compounding ratio (A/B) of the organic low molecular weight material (A) to the organic low molecular weight material (B) is in the range of from 95/5 to 5/95, preferably from 90/10 to 30/70, and more preferably from 85/15 to 50/50 by weight ratio. If the compounding ratio of the organic low molecular weight material (B) to the organic low molecular weight material (A) is too small, the temperature range of making the reversible heat-sensitive recording layer transparent is not enlarged, and if the compounding ratio is too large, the contrast is greatly lowered, which are both undesirable.

The proportion of the organic low Imolecular weight material (A) to the resin matrix is preferably from 0.5 to 50 parts by weight per 100 parts by weight of the resin matrix. If the proportion of the organic low molecular weight material (A) is less than the above-described range, a sufficient contrast is not obtained, and if the proportion is larger than the range, a sufficient film-forming property is not obtained, which are both undesirable.

The proportion of the organic low molecular weight material (B) to the resin matrix is preferably from 0.5 to 50 parts by weight per 100 parts by weight of the resin matrix. If the proportion of the organic low molecular weight material (B) is less than the above-described range, the orienting property cannot be imparted to the melt of the organic low molecular weight material (A). On the other hand, if the proportion is over the above range, the amount of the organic low molecular weight material (B) exceeds the compatible limit for the resin matrix, whereby the contrast is lowered and a sufficient film-forming property is not obtained.

Furthermore, the proportion of the total amount of the organic low molecular weight materials (A) and (B) to the resin matrix is preferably from 10 to 150 parts by weight per 100 parts by weight of the resin matrix. If the proportion of the total amount of the organic low molecular weight materials is less than the above-described range, a sufficient contrast is not obtained and if the proportion is over 150 parts by weight, the strength of the coated film is lowered and the low molecular weight materials deposit on the surface, which are undesirable.

For the formation of the heat-sensitive recording layer, generally, a solution is prepared by dissolving the resin matrix and two components of the organic low molecular weight materials in a solvent or a solution of the resin matrix is prepared using a solvent which does not dissolve at least one of the organic low molecular weight materials, following by dispersing in the solution the organic low molecular weight material in a fine particle form, and the solution or the dispersion is coated on the substrate and dried to form a heat-sensitive recording layer. Further, the resin matrix is cured by thermal crosslinking under a proper heat-treatment condition.

The solvent used to form the heat-sensitive recording layer may be properly selected according to the kinds of the resin matrix and the organic low molecular weight materials, and the examples thereof are tetrahydrofuran, methyl ethyl ketone, methyl isobutyl ketone, chloroform, carbon tetrachloride, methanol, ethanol, toluene, and benzene.

The layer thickness of the heat-sensitive layer is in the range of usually from 8 to 38 μm, and preferably from 10 to 30 μm. If the layer thickness is larger than the above-described range, the sensitivity is lowered and since the temperature gradient occurs in the thickness direction, a sufficient white turbidity is not obtained, which is undesirable in the present invention. On the other hand, if the layer thickness is smaller than 8 82 m, the contrast is undesirably lowered.

The recording medium of the present invention may further, if necessary, contains a lubricant, an antistatic agent, a plasticizer, a dispersing agent, a stabilizer, a surface active agent, an inorganic or organic filler, etc.

On the heat-sensitive recording layer may further form, if necessary, an overcoat layer directly or via an undercoat layer to protect the recording layer. For the overcoat layer, an organic material such as acrylic material, a silicone type material, a fluorine type organic material, a urethane type materials, etc., may be used or an inorganic material such as $SiO_2$, SiO, MgO, ZnO, $TiO_2$, $Al_2O_3$, $Ta_2O_5$, etc., may be used.

The resin which is used for the overcoat layer may also be a thermosetting resin, an electron ray curable resin, or an ultraviolet curable resin.

For forming the overcoat layer, a conventional coating method or vacuum thin film-forming method (vacuum vapor deposition method, etc.) is used, and the thickness of the overcoat layer is from 0.1 to 5.0 μm, and preferably from 1.0 to 3.0 μm. If the thickness of the overcoat layer is smaller than the above-described range, the protective effect is insufficient and if the thickness is larger than the range, the amount of the energy required for recording becomes larger, which are both undesirable.

Further, to improve the durability of the reversible heat-sensitive recording layer, an interlayer may be formed between the recording layer and the overcoat layer.

For the interlayer, thermoplastic resins such as polyvinyl chloride, a vinyl chloride-vinyl acetate copolymer, polyvinylidene chloride, polyester, polyamide, polyacrylate, polymethacrylate, polystyrene, nitrocellulose, ethyl cellulose, polyvinyl alcohol, polyvinyl butyral, etc.; thermosetting resins such as a polyimide resin, a polyurethane resin, etc.; or photosetting resins with ultraviolet rays, electron rays, etc., may be used. In this case, by the same reason as in the overcoat layer, the thickness of the interlayer is preferably from 0.1 to 5.0 μm, and more preferably from 0.1 to 3.0 μm.

A coloring material which can be used for the colored layer formed on the other surface of the substrate can be any materials which are conventionally used in the art of this field. For example, gravure inks, Flexo inks, lithographic inks, etc., formed by dispersing pigments or dyes in an acrylic binder, a urethane binder, an epoxy binder, a vinyl chloride binder, a cellulose binder, etc., can be used.

The color of the colored layer can be properly selected from black, blue, red, green, brown, and purple. In these colors, a relatively dark color is preferred so as to increase the contrast.

Further, by compounding a magnetic substance with the colored layer of the reversible heat-sensitive recording medium of the present invention to give also the function as a magnetic material layer, a magnetic card capable of reversible heat-sensitive recording may be prepared. In this case, if the reversible heat-sensitive recording layer is formed on one surface of the substrate and the magnetic material layer is formed on the other surface of the substrate, a magnetic card wherein white turbid characters are recorded with the color (black to brown) of the magnetic substance as a background is obtained.

For such a colored layer, a conventional magnetic coating composition is used. As the magnetic substance in the magnetic coating composition, for example, magnetic iron oxide is used and $\gamma$-$Fe_2O_3$ is particularly preferred.

Further, if necessary, the colored layer may contain various additives such as a plasticizer, a lubricant, a dispersing agent, an antistatic agent, a crosslinking agent, etc.

Figure 2A:
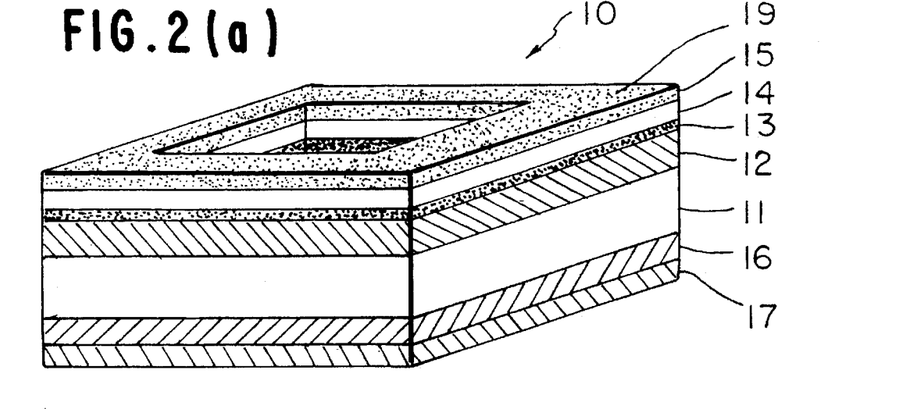
FIGS. 2(a) and 2(b) are schematic cross sectional views showing one example of the magnetic card of the present invention.
Figure 2B:
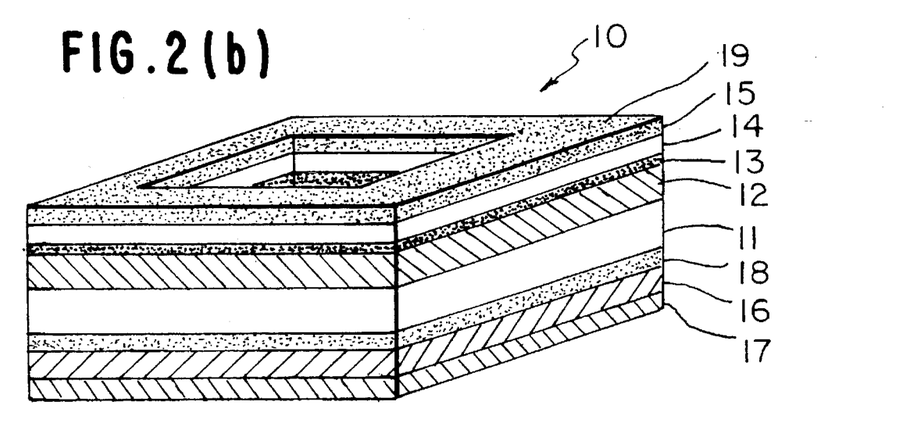

The reversible heat-sensitive recording medium of the present invention can be used by adhering the same to an IC card using an adhesive, etc., in addition to as a magnetic card. In this case, the reversible heat-sensitive recording layer may be formed on any surface side of the IC card. Further, the reversible heat-sensitive recording medium may be adhered to the entire surface of the IC card or a part of the surface of the card. The card having the reversible heat-sensitive recording layer can be utilized in a wide field such as highway cards, various kinds of prepaid cards used in department stores, super stores, etc., JR orange cards, stored fare cards, commutation tickets, etc. FIGS. 2(a) and (b) show schematic cross sectional views of one example of the magnetic card of the present invention. In FIG. 2 (a), a magnetic card 10 has a transparent substrate 11, a reversible heat-sensitive recording layer 12 formed on one surface of the substrate, an overcoat layer 13 formed on the reversible heat-sensitive recording layer, a white hiding layer 14 formed on the overcoat layer, and a printed layer 15 formed on the white hiding layer. In this case, the printed layer 15 is formed excluding a display area portion 19. The magnetic card further 10 further has a magnetic material layer 16 serving also as a colored layer formed on the other surface of the transparent substrate 11 and a hiding layer 17 formed on the magnetic material layer.

In the example shown in FIG. 2(b), the colored layer and the magnetic material layer are formed separately different from the example of FIG. 2(a). That is, a colored layer 18 is formed on the other surface of the transparent substrate 11, and the magnetic material layer 16 and the hiding layer 17 are formed on the colored layer.

The preferred coating composition used for the white hiding layer is a coating composition obtained by compounding a pigment such as $TiO_2$, $SiO_2$, $Al_2O_3$, etc.; a binder such as a vinyl chloride resin, a urethane resin, an epoxy resin, an acrylic resin, etc., and, if necessary, a solvent such as toluene, methyl ethyl ketone, cyclohexanone, ethyl acetate, xylene, etc.

For forming the white hiding layer, a conventional coating method or printing method such as a screen printing method, an offset printing method, a gravure printing method, etc., is used, and the dry thickness of the layer is preferably from 0.1 to 10 μm. If the thickness of the white hiding layer is smaller than 0.1 μm, the color of its under layer cannot be undesirably hided and if the thickness is larger than 10 μm, it undesirably causes the occurrences of curling and cracks.

A coating composition used for the printed layer and the hiding layer formed on the other surface of the substrate is preferably a coating composition obtained by compounding a conventional inorganic or organic pigment (or dye), a binder such as a vinyl chloride resin, a urethane resin, an epoxy resin, an acrylic resin, etc., and, if necessary, a solvent such as toluene, methyl ethyl ketone, cyclohexanone, ethyl acetate, xylene, etc. For forming these printed layer and hiding layer, the same method as the case of forming the white hiding layer described above may be used.

The dry thickness of the printed layer is preferably in the range of from 0.1 to 10 μm and the dry thickness of the hiding layer is preferably in the range of from 0.1 to 20 μm.

For all the layers described above, a thermoplastic resin, a light (including electron rays, ultraviolet rays, etc.) setting resin, a thermosetting resin, etc., may be used, and a light setting resin and a thermosetting resin are particularly preferred.

At the formation of the magnetic card of the present invention, an adhesive layer may be formed between respective layers of the substrate, the reversible heat-sensitive recording layer, the overcoat layer, the white hiding layer, the colored layer, and the magnetic material layer for the purpose of improving the adhesion between the layers.

The reversible heat-sensitive recording medium of the present invention is practically described by the following examples, in which all parts are by weight.

EXAMPLE 1

A transparent polyethylene terephthalate film (hereinafter referred to as "PET film") of 100 μm in thickness was used as a substrate, and a black ink (CGL-325, trade name, made by Sakata Inks K. K.) was coated on one surface thereof at a dry thickness of 10 μm by a wire bar and dried to form a colored layer.

A coating composition for a reversible heat-sensitive recording layer having the composition shown below was coated on the other surface of the substrate at a dry thickness of 20 μm followed by heating, and the coated layer was then aged at 60° C. for 24 hours to perform thermal crosslinking of the recording layer. The proportion of the total amount of the organic low molecular weight materials (behenic acid + thiodipropionic acid) in the reversible heat-sensitive recording layer to the resin matrix (a vinyl chloride-vinyl acetate-hydrocypropyl acrylate copolymer) was that the total amount of the organic low molecular weight materials was 40 parts per 100 parts of the resin matrix.

| Reversible heat-sensitive recording layer composition | |
|---|---|
| Behenic acid | 7 parts |
| Thiodipropionic acid | 3 parts |
| Vinyl chloride-vinyl acetate-hydroxypropyl acrylate copolymer (TA2, made by Nisshin Kagaku K.K.) | 25 parts |
| 1,3-Pentadiene copolymer | 2 parts |
| Isocyanate crosslinking agent (Coronate L, trade name, made by Nippon Polyurethane K.K.) | 3 parts |
| Tetrahydrofuran | 120 parts |

A coating solution composed of an acrylic ultraviolet curable resin (BR-370, trade name, made by Asahi Denka Kogyo K. K.) and 50 parts of methanol was coated on the recording layer at a dry thickness of 2 μm as a overcoat layer and cured by the irradiation with ultraviolet rays of 500 mj/cm$^2$.

The reversible heat-sensitive recording medium thus prepared was printed using a line-type thermal head (8 dots/mm, printing energy: 0.6 mJ/dot), and the contrast and the visibility were determined.

The contrast was shown by the difference between the optical reflection density at the printed portion and the optical reflection density at the nonprintedportion with a Macbeth densitometer (Model RD-920). Further, the angle dependency was evaluated such that the recorded prints were observed from various angles under a fluorescent lamp and the easiness to see the recorded charcters was visually evaluated. Furthermore, the visibility was visually evaluated by a total seeing easiness by taking into consideration the contrast and the angle dependency.

EXAMPLE 2

By following the same procedure as in Example 1 except that a transparent PET film of 188 μm in thickness was used as the substrate, a reversible heat-sensitive recording medium was prepared and evaluated as in Example 1.

EXAMPLE 3

By following the same procedure as in Example 1 except that a transparent PET film was used as the substrate, and the following magnetic material was coated at a dry thickness of 15 m as the colored layer, a reversible heat-sensitive recording medium was prepared and evaluated.

| Magnetic material (colored layer composition) | |
|---|---|
| γ-Fe$_2$O$_3$ | 40 parts |
| Vinyl chloride-vinyl acetate-polyvinyl alcohol copolymer | 20 parts |
| Unsaturated polyester resin (Baylon 103, trade name, made by TOYOBO Co., Ltd.) | 5 parts |
| Polyurethane elastomer (made by Nippon Polyurethane K.K.) | 7 parts |
| Oleic acid | 5 parts |
| Toluene | 60 parts |
| Methyl isobutyl ketone | 60 parts |
| Isocyante crosslinking agent (Coronate HL, trade name, made by Nippon Polyurethane K.K.) | 5 parts |
| Triethylenediamine | 0.5 parts |

EXAMPLE 4

By following the same procedure as in Example 1 except that the layer thickness of the reversible heat-sensitive recording layer was increased to 10 μm, a reversible heat-sensitive recording medium was prepared and evaluated as in Example 1.

EXAMPLE 5

By following the same procedure as in Example 1 except that the layer thickness of the reversible heat-sensitive recording layer was increased to 30 μm, a reversible heat-sensitive recording medium was prepared and evaluated as in Example 1.

EXAMPLE 6

By following the same procedure as in Example 1 except that the coating composition for the reversible heat-sensitive layer was prepared with the following composition, a reversible heat-sensitive recording medium was prepared and evaluated as in Example 1. The proportion of the total amount of the organic low molecular weight materials (behenic acid + thiopropionic acid) in the reversible heat-sensitive recording layer to the resin matrix (a vinyl chloride-vinyl acetate-hydroxypropyl acrylate copolymer) was that the total amount of the organic low molecular weight materials was 140 parts per 100 parts of the resin matrix.

| Reversible heat-sensitive recording layer composition | |
|---|---|
| Behenic acid | 24.5 parts |
| Thiodipropionic acid | 10.6 parts |
| Vinyl chloride-vinyl acetate-hydroxypropyl acrylate (TA2, trade name, made by Nissin Kagaku K.K.) | 25 parts |
| 1,3-Pentadiene copolymer | 2 parts |
| Isocyanate crosslinking agent (Coronate, trade name, made by Nippon Polyurethane K.K.) | 3 parts |
| Tetrahydrofuran | 195 parts |

EXAMPLE 7

By following the same procedure as in Example 1 except that the coating composition for the reversible heat-sensitive layer was prepared with the following composition, a reversible heat-sensitive recording medium was prepared and evaluated as in Example 1. The proportion of the total amount of the organic low molecular weight materials (behenic acid + thiopropionic acid) in the reversible heat-sensitive recording layer to the resin matrix (a vinyl chloride-vinyl acetate-hydroxypropyl acrylate copolymer) was that the total amount of the organic low molecular weight materials was 80 parts per 100 parts of the resin matrix.

| Reversible heat-sensitive recording layer composition | |
|---|---|
| Behenic acid | 14 parts |
| Thiodipropionic acid | 6 parts |
| Vinyl chloride-vinyl acetate-hydroxypropyl acrylate (TA2, trade name, made by Nissin Kagaku K.K.) | 25 parts |
| 1,3-Pentadiene copolymer | 2 parts |
| Isocyanate crosslinking agent (Coronate, trade name, made by Nippon Polyurethane K.K.) | 3 parts |
| Tetrahydrofuran | 150 parts |

EXAMPLE 8

| Hiding layer composition | |
|---|---|
| Aluminum powder | 30 parts |
| Vinyl chloride-vinyl acetate-vinyl alcohol copolymer | 50 parts |
| Methyl ethyl ketone | 200 parts |
| Toluene | 50 parts |

Figure 3:
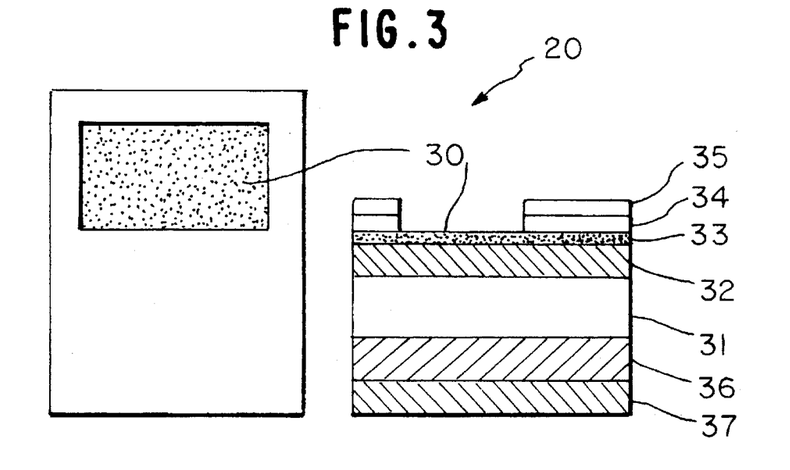
FIG. 3 is a plain view and a cross sectional view of the magnetic card of the present invention prepared in Example 8.

As shown in FIG. 3, the solution having the composition described above was coated on the surface of the magnetic material layer 36 of the reversible heat-sensitive recording medium prepared in the same manner as in Example 3 with a roll coater. The coated layer was dried at 100° C. for 2 minutes to form a hiding layer 37 of 10 μm in thickness. On the other hand, an ultraviolet curable white ink was coated as a print on the side of the overcoat layer 33 excluding the display area 30 using an offset printer and then irradiated with ultraviolet rays (irradiation energy: 500 mJ/cm$^3$) to form a white hiding layer 34. Further, a printed layer 35 was formed on the surface of the white hiding layer 34 excluding the display area 30 using ultraviolet curable inks of 4 colors (red, blue, yellow, and black) to obtain a magnetic card 20. When the magnetic card thus prepared was evaluated by the same methods as in Example 1, good results were obtained.

COMPARATIVE EXAMPLE 1

By following the same procedure as in Example 1 except that a PET film of 100 μm was used as a substrate and after applying on the surface of the substrate an aluminum vapor deposition layer (thickness: 500 Å) to form a metal reflective layer, the same reversible heat-sensitive layer as in Example 1 was formed on the metal layer, a reversible heat-sensitive recording medium was prepared and evaluated as in Example 1.

COMPARATIVE EXAMPLE 2

By following the same procedure as in Example 1 except that a PET film of 100 μm in thickness was used as the substrate and after forming the colored layer as in Example 1 on one surface of the colored layer, the reversible heat-sensitive recording layer as in Example 1 was formed thereon, a reversible heat-sensitive recording medium was prepared and evaluated as in Example 1.

COMPARATIVE EXAMPLE 3

By following the same procedure as in Example 1 except that a PET film of 25 μm in thickness was used as the substrate, a reversible heat-sensitive recording medium was prepared and evaluated as in Example 1.

COMPARATIVE EXAMPLE 4

By following the same procedure as in Example 1 except that the layer thickness of the reversible heat-sensitive recording layer was 7 μm, a reversible heat-sensitive recording medium was prepared and evaluated as in Example 1.

COMPARATIVE EXAMPLE 5

By following the same procedure as in Example 1 except that the layer thickness of the reversible heat-sensitive recording layer was 40 μm, a reversible heat-sensitive recording medium was prepared and evaluated.

COMPARATIVE EXAMPLE 6

By following the same procedure as in Example 1 except that the reversible heat-sensitive recording layer having the following composition was formed, a reversible heat-sensitive medium was prepared and evaluated as in Example 1.

The proportion of the total amount of the organic low molecular weight materials (behenic acid + thiopropionic acid) in the reversible heat-sensitive recording layer to the resin matrix (a vinyl chloride-vinyl acetate-hydroxypropyl acrylate copolymer) was that the total amount of the organic low molecular weight materials was 180 parts per 100 parts of the resin matrix.

| Reversible heat-sensitive recording layer composition | |
|---|---|
| Behenic acid | 31.5 parts |
| Thiodipropionic acid | 13.5 parts |
| Vinyl chloride-vinyl acetate-hydroxypropyl acrylate copolymer (TA2, trade name, made by Nisshin Kagaku K.K.) | 25 parts |
| 1,3-Pentadiene copolymer | 2 parts |
| Isocyanate crosslinking agent (Coronate, trade name, made by Nippon Polyurethane K.K.) | 3 parts |
| Tetrahydrofuran | 225 parts |

COMPARATIVE EXAMPLE 7

By following the same procedure as in Example 1 except that the reversible heat-sensitive recording layer having the following composition was formed, a reversible heat-sensitive recording medium was prepared and evaluated as in Example 1.

The proportion of the total amount of the organic low molecular weight materials (behenic acid + thiodipropionic acid) in the reversible heat-sensitive recording layer to the resin matrix (a vinyl chloride-vinyl acetate-hydroxypropyl acrylate copolymer) was that the total amount of the organic low molecular weight materials was 8 parts per 100 parts of the resin matrix.

| Reversible heat-sensitive recording layer composition | |
|---|---|
| Behenic acid | 1.4 parts |
| Thiodipropionic acid | 0.6 part |
| Vinyl chloride-vinyl acetate-hydroxypropyl acrylate copolymer (TA2, trade name, made by Nisshin Kagaku K.K.) | 25 parts |
| 1,3-Pentadiene copolymer | 2 parts |
| Isocyanate crosslinking agent (Coronate, trade name, made by Nippon Polyurethane K.K.) | 3 parts |
| Tetrahydrofuran | 96 parts |

TABLE 1

| | Contrast | Angle Dependency | Visibility*[1] |
|---|---|---|---|
| Example 1 | 0.80 | None | ○ |
| Example 2 | 0.85 | None | ⊙ |
| Example 3 | 1.00 | None | ⊙ |
| Example 4 | 0.75 | None | ○ |
| Example 5 | 1.20 | None | ⊙ |
| Example 6 | 1.02 | None | ⊙ |
| Example 7 | 0.93 | None | ⊙ |
| Comparative Example 1 | 0.90 | Exist | x |
| Comparative Example 2 | 0.60 | None | △ |
| Comparative Example 3 | 0.65 | None | △ |
| Comparative Example 4 | 0.50 | None | x |
| Comparative Example 5 | 0.55 | None | △ |
| Comparative Example 6 | 0.61 | None | △ |
| Comparative Example 7 | 0.29 | None | △ |

*[1] ⊙: Very good
○: Good
△: Slightly difficult to see
x: Difficult to see

COMPARATIVE EXAMPLE 8

By following the same procedure as in Example 1 except that a reversible heat-sensitive recording layer having the following composition (no crosslinking agent) was formed as a comparative example wherein the reversible heat-sensitive recording layer was not thermally crosslinked, a reversible heat-sensitive recording medium was prepared.

| Reversible heat-sensitive recording layer composition (no crosslinking agent) | |
|---|---|
| Behenic acid | 7 parts |
| Thiopropionic acid | 3 parts |
| Vinyl chloride-vinyl acetate copolymer (VYHH, trade name, made by UCC Co.) | 25 parts |
| 1,3-Pentadiene copolymer | 2 parts |
| Tetrahydrofuran | 120 parts |

When printing/erasing were repeatedly applied to the same portion as to the sample of Comparative Example 8 and the sample of Example 1 described above, the durability of the samples was evaluated. The energy of the thermal head used for the evaluation was 0.6 mj/dot and the erasion was carried out by contacting a stamp heated to 80° C. for one second. The results obtained are shown in FIG. 4.

Figure 4:
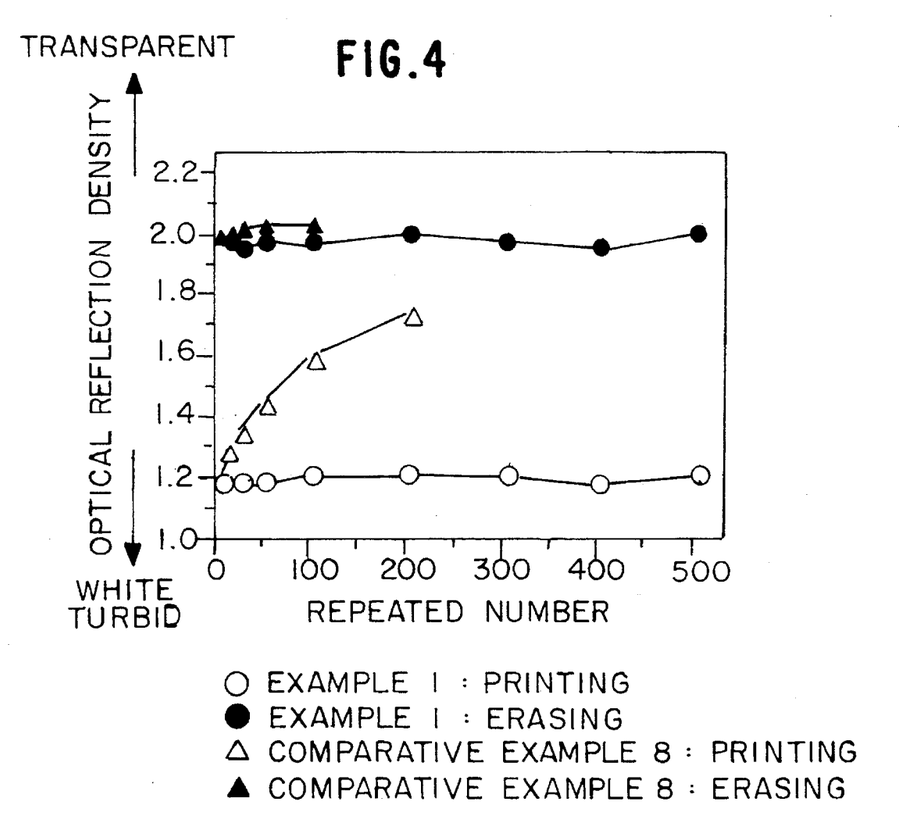
FIG. 4 is a graph showing the change of optical reflection densities by repeating printing/erasing of reversible heat-sensitive recording media.

In FIG. 4, the vertical axis shows the optical reflection density measured by a Macbeth densitometer (Model RD-920) and the horizontal axis shows the repeated number. In addition, in the vertical axis, a higher numerical value shows a higher transparency and a lower numeral value shows a higher white tubidity.

In the reversible heat-sensitive recording medium of the present invention, the contrast is higher than conventional ones and the visibility is greatly improved. Further, when the reversible heat-sensitive recording layer is thermally crosslinked, the heat resistance thereof is improved.

While the invention has been described in detail and with reference to specific embodiments thereof, it will be apparent to one skilled in the art that various changes and modifications can be made therein without departing from the spirit and scope thereof.

What is claimed is:

1. A reversible heat-sensitive recording medium comprising a transparent substrate having a reversible heat-sensitive recording layer formed on one surface of the substrate and having a colored layer formed on the other surface of the substrate, wherein the reversible heat-sensitive recording layer contains organic low molecular weight materials and a crosslinked resin matrix, and prints in a white turbid state and erases in a transparent state, and the colored layer contains a magnetic material.

2. A reversible heat-sensitive recording medium of claim 1, wherein the reversible heat-sensitive recording layer contains from 10 to 150 parts by weight of the organic low molecular weight materials per 100 parts by weight of the crosslinked resin matrix.

3. A reversible heat-sensitive recording medium of claim 1, wherein the organic low molecular weight materials contain (A) at least one compound selected from the group consisting of a higher fatty acid having at least 16 carbon atoms and a ketone having a melting point of at least 50° C., and (B) at least one compound selected from the group consisting of an aliphatic saturated dicarboxylic acid and a sulfide represented by the formula $$HOOC(CH_2)_m\text{-}S\text{-}(CH_2)_nCOOH$$

wherein m and n each is an integer of from 1 to 5, and the compounding ratio (A/B) of the organic low molecular weight compound (A) to the organic low molecular weight compound (B) is from 85/15 to 50/50.

4. A reversible heat-sensitive recording medium of claim 1, wherein the substrate is a transparent plastic having a thickness of at least 30 μm.

5. A reversible heat-sensitive recording medium of claim 1, wherein the reversible heat-sensitive recording layer has a thickness of from 8 to 38 μm.

* * * * *